United States Patent [19]
Woudenberg et al.

[11] Patent Number: 5,942,636
[45] Date of Patent: Aug. 24, 1999

[54] PROCESS OF PREPARING 2-ALKYL-2,3-DIHYDRO-1H-BENZ [E]INDENE-1-ONE DERIVATIVES

[75] Inventors: Richard Herman Woudenberg, Elst; Heert Andringa, Deventer, both of Netherlands

[73] Assignee: Akzo Nobel N.V., Netherlands

[21] Appl. No.: 09/012,164

[22] Filed: Jan. 22, 1998

[30] Foreign Application Priority Data

Apr. 2, 1997 [EP] European Pat. Off. ............. 97200302

[51] Int. Cl.[6] .............................. C07F 17/00; C07F 7/00; C07C 45/00
[52] U.S. Cl. .................... 556/11; 556/8; 556/12; 568/323; 568/328
[58] Field of Search ................... 568/323, 328; 556/8, 11, 12

[56] References Cited

U.S. PATENT DOCUMENTS 5,455,366 10/1995 Rohrmann et al. .................. 556/8

FOREIGN PATENT DOCUMENTS 0 629 631 12/1994 European Pat. Off. .

OTHER PUBLICATIONS

*European Search Report*, dated Jun. 16, 1997.

Udo Stehling, Josef Diebold, Robin Kirsten, Werner Roll, and Hans–erbert Brintzinger, "ansa–Zirconocene Polymerization Catalysts with Annelated Ring Ligands–Effects on Catalytic Activity and Polymer Chain Length" vol. 13, *Organometallics* pp. 964–970 (1994).

Jaysukhlal R. Merchant, Ravindra B. Upasani, "Synthesis of substituted benzindanones" vol. 19, *Chemistry and Industry* p. 929, Dec. 1983.

*Primary Examiner*—Porfirio Nazario-Gonzalez
*Attorney, Agent, or Firm*—Richard P. Fennelly

[57] ABSTRACT

The invention relates to a process of preparing a 2-alkyl-2,3-dihydro-1H-benz[e]indene-1-one derivative, preferably 2,3-dihydro-2-methyl-benz[e]indene-1-one, characterized in that a naphthalene derivative is condensed with an active ester of 2-alkyl-2-propenoic acid, preferably with 2-methyl-2-propenoyl chloride. The product which is obtained in high yield and substantially free from its isomer is an intermediate in the preparation of rac-dimethyl bis(2-alkyl-1H-benz[e]indenyl)silandiyl zirconium dichloride complex.

8 Claims, No Drawings

PROCESS OF PREPARING 2-ALKYL-2,3-DIHYDRO-1H-BENZ [E]INDENE-1-ONE DERIVATIVES

FIELD OF THE INVENTION

The invention generally relates to a process of preparing 2-alkyl-2,3-dihydro-1H-benz[e]indene-1-one derivatives, in particular to the preparation of 2,3-dihydro-2-methyl-1H-benz[e]indene-1-one, and further to the preparation of 2-methyl-1H-benz[e]indene and rac-dimethyl bis(2-methyl-1H-benz[e]indenyl)silandiyl zirconium dichloride complex from said 2,3-dihydro-2-methyl-benz[e]indene-1-one.

BACKGROUND OF THE INVENTION

2-Alkyl-2,3-dihydro-1H-benz[e]indene-1-one derivatives are interesting intermediates in the preparation of metallocenes, which are applied as catalysts in the manufacture of high-molecular weight polyolefins with high isotactic properties. Various methods for the preparation of 2-alkyl-2,3-dihydro-1H-benz[e]indene-1-one derivatives are known in the art. For instance, U. Stehling et al., *Organometallics*, Vol. 13 (3), 964–70 (1994) disclose a method in which naphthalene is condensed with 2-bromo-2-methylpropanoyl bromide. The method provides a mixture of 2,3-dihydro-2-methyl-1H-benz[e]indene-1-one and 1,2-dihydro-2-methyl-3H-benz[e]indene-3-one. Drawbacks of this method are the relatively low yield (74%) and the mixture of benz[e]indene isomers which is obtained and which can only be separated and purified by expensive column chromatography. This means that in follow-up steps also mixtures are obtained, and that the final product must be purified of its contaminants, which is a laborious and expensive procedure.

J. R. Merchant and R. B. Upasani, *Chem. Ind.*, 929 (1983), prepared a mixture of benz[e]indene-1-one and benz[e]indene-3-one derivatives from 1,6-dimethoxynaphthalene and acrylic acid in the presence of polyphosphorous acid, which mixture was not separated.

In a method disclosed in U.S. Pat. No. 5,455,366, 2-methyl-3-naphthylpropionic acid was cyclized using thionyl chloride. This method does not lead to a mixture of isomers, but it has the disadvantages that expensive silica gel chromatography purification is necessary and that unacceptably low yields are obtained (45%). Other known methods suffer from one or more of the same drawbacks, i.e. low yields, laborious and expensive purifications, and the occurrence of mixtures of isomers.

Many methods for obtaining 1-indanone and derivatives thereof have been disclosed. However, because ring closure of phenylpropanone or derivatives thereof usually does not give rise to a mixture of isomers, these methods do not give any indication of the selectivity of such reactions. Moreover, the few methods for the synthesis of indene derivatives from substituted phenyl derivatives which have been disclosed, also lead to mixtures. For instance, EP 629,631 describes the ring closure of p-cymene with 2-methyl-2-propenoyl chloride, which leads to a mixture of isomers in a low yield (67%). The respective α and β positions in naphthalene are the reason for the occurrence of a mixture of isomers.

The present invention therefore provides a novel method circumventing all of the above-mentioned disadvantages. In its most general concept, the invention concerns a process of preparing a 2-alkyl-2,3-dihydro-1H-benz[e]indene-1-one derivative, characterized in that a naphthalene derivative is condensed with an active ester of 2-alkyl-2-propenoic acid. The method provides a high yield, a better than 95% selectivity, and a simple and inexpensive purification method by crystallization.

SUMMARY OF THE INVENTION

The invention generally relates to a process of preparing 2-alkyl-2,3-dihydro-1H -benz[e]indene-1-one derivatives, particularly 2,3-dihydro-2-methyl-1H-benz[e]indene-1-one. The invention further relates to the preparation of 2-methyl-1H-benz[e]indene and rac-dimethyl bis(2-methyl-1H-benz[e]indenyl) silandiyl zirconium dichloride complex from said 2,3-dihydro-2-methyl-benz[e]indene-1-one.

DETAILED DESCRIPTION OF THE INVENTION

This process is performed in a manner analogous to the conversion of similar aromatic compounds with an active ester of 2-alkyl-2-propenoic acid. This type of reaction is generally known as a Friedel-Crafts reaction. Suitable catalysts are Lewis acids such as aluminum-, iron (III)-, tin (IV)-, and boron-halides, in particular aluminum chloride, iron(III) chloride, and boron trifluoride. Aluminum chloride is the most preferred catalyst. The reaction can be performed in carbon disulfide, chloroform, dichloromethane, and other suitable solvents which are known in the art. The condensation step of the presently claimed process is preferably performed at a temperature lower than 0° C., more preferably at a temperature between −15° C. and −80° C. A very suitable reaction temperature is about −30° C., which provides high yields, high selectivity, and short reaction times.

The term "naphthalene derivative" means naphthalene or a naphthalene substituted with ($C_1$–$C_6$) alkyl, ($C_1$–$C_6$) alkoxy, halogen, or hydroxy. Accordingly, the term "2-alkyl-2,3-dihydro-1H-benz[e]indene-1-one derivative" means 2-alkyl-2,3-dihydro-1H-benz[e]indene-1-one or a 2-alkyl-2,3-dihydro-1H-benz[e]indene-1-one of which the naphthalene moiety of the molecule is substituted with ($C_1$–$C_6$) alkyl, ($C_1$–$C_6$) alkoxy, halogen, or hydroxy. The term "alkyl" in 2-alkyl-2-propenoic acid means ($C_1$–$C_6$) alkyl. The term ($C_1$–$C_6$) alkyl means a branched or unbranched alkyl group with 1 to 6 carbon atoms, such as methyl, ethyl, propyl, isopropyl, t-butyl, hexyl, and the like. Methyl is the preferred alkyl group.

The term "halogen" means fluorine, chlorine, bromine, or iodine.

The term "active ester" means any group that can be displaced from a carbonyl group, such as tosyl, symmetric or unsymmetric anhydride, succinimide, halogen, and the like. The most preferred active ester of 2-alkyl-2-propenoic acid is 2-methyl-2-propenoyl halide, particularly 2-methyl-2-propenoyl chloride.

The invention further relates to a process of preparing 2-alkyl-1H-benz[e]indene, characterized in that naphthalene is condensed with a 2-alkyl-2-propenoyl halide, and preferably with 2-methyl-2-propenoyl chloride, according to the above-mentioned process, after which the 2-alkyl-2,3-dihydro-1H-benz[e]indene-1-one obtained is converted to 2-alkyl-1H-benz[e]indene.

Such conversion can be performed by methods known in the art for the reduction of ketones to unsaturated hydrocarbons. Suitable methods are, for instance, Zn reduction under alkaline conditions or, preferably, reduction with metal hydrides, such as lithium aluminum hydride or sodium borohydride. The resulting hydroxy intermediate is dehydrated under acidic or alkaline conditions, which is a standard procedure and known to the artisan.

In a further aspect, the invention relates to a process of preparing rac-dimethyl bis(2-alkyl-1H-benz[e]indenyl) silandiyl zirconium dichloride complex, characterized in that naphthalene is condensed with a 2-alkyl-2-propenoyl halide, preferably with 2-methyl-2-propenoyl chloride, after which the 2-alkyl-2,3-dihydro-1H-benz[e]indene-1-one obtained is converted to 2-alkyl-1H-benz[e]indene according to the above-mentioned process, first followed by conversion to dimethyl bis(2-alkyl-1H-benz[e]-indenyl) silane, and then by conversion to rac-dimethyl bis(2-alkyl-1H-benz

[e]-indenyl)silandiyl zirconium dichloride complex according to methods known per se.

The conversion of 2-alkyl-2,3-dihydro-1H-benz[e]indene-1-one to rac-dimethyl bis(2-alkyl-1H-benz[e]indenyl)silandiyl zirconium dichloride complex has been disclosed in U. Stehling et al., *Organometallics,* Vol. 13 (3), 964–70 (1994), with methyl as the alkyl group. For alkyl groups other than methyl, the synthesis can be performed in a similar manner.

The intermediates in the above-mentioned process for the preparation of rac-dimethyl bis(2-alkyl-1H-benz[e]indenyl)silandiyl zirconium dichloride complex may be isolated, but may also be further processed in situ.

The invention is further illustrated by the following example.

EXAMPLE 2,3-Dihydro-2-methyl-1H-benz[e]indene-1-one

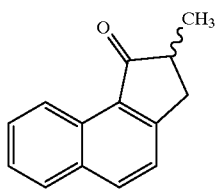

Aluminum chloride powder (240 g) was added to a dry round-bottomed flask under nitrogen, after which 1 l of dichloromethane was added. The suspension was cooled to −30° C., and 100 g of naphthalene and 90.5 g of freshly distilled 2-methyl-2-propenoyl chloride in 950 ml of dichloromethane were added dropwise under nitrogen in 1.5 h. The reaction mixture was stirred for another hour at −30° C., after which the cold reaction mixture was poured into 10 l of ice water. The organic layer was separated, the water layer was extracted with dichloromethane, and the combined organic layers were washed with brine, dried over magnesium sulfate, and evaporated to dryness. The crude product was distilled at 200° C./33 Pa, after which 127 g (84%) of 2,3-dihydro-2-methyl-1H-benz[e]indene-1-one were obtained with a purity >95% (GLC).

2,3-Dihydro-1-hydroxy-2-methyl-1H-benz[e]indene

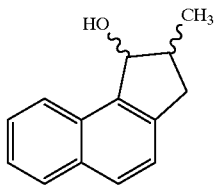

Sodium borohydride (7.5 g) was added portion-wise at 0–20° C. to a solution of 18.1 g of 2,3-dihydro-2-methyl-benz[e]indene-1-one in 200 ml of methanol. The reaction was completed after 15 min of stirring, and the reaction mixture was poured into 400 ml of water. The organic layer was separated, and the water layer was extracted with diethyl ether. The combined organic layers were washed with water and brine, dried over magnesium sulfate, and evaporated to dryness. The crude product was recrystallized from cyclohexane to obtain 14.3 g (78%) of 2,3-dihydro-1-hydroxy-2-methyl-1H-benz[e]indene.

2-Methyl-1H-benz[e]indene

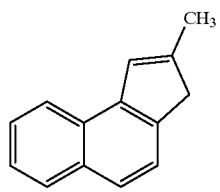

A solution of 15.0 g of oxalic acid monohydrate in 100 ml of toluene was refluxed under nitrogen, and the water was removed by azeotropic distillation. To the dried oxalic acid solution 14.7 g of 2,3-dihydro-1-hydroxy-2-methyl-1H-benz[e]indene in 50 ml of toluene were added, and the water formed was removed by azeotropic distillation in 2 h. After cooling, the oxalic acid was removed by filtration and the filter cake was washed with toluene. The combined toluene layers were washed with sodium hydrogencarbonate and brine, dried over magnesium sulfate, and evaporated to dryness. The crude product was distilled at 175° C./100 Pa, after which 11.8 g (88%) of 2-methyl-1H-benz[e]indene were obtained.

We claim:

1. A process of preparing a 2-alkyl-2,3-dihydro-1H-benz[e]indene-1-one derivative which comprises condensing a naphthalene derivative with 2-methyl-2-propenoyl chloride.

2. The process of claim 1 wherein naphthalene is condensed with 2-methyl-2-propenoyl chloride.

3. A process of preparing 2-alkyl-1H-benz[e]indene which comprises condensing naphthalene with a 2-alkyl-2-propenoyl chloride according to the process of claim 1 after which the 2-alkyl-2,3-dihydro-1H-benz[e]indene-1-one obtained is converted to 2-alkyl-1H-benz[e]indene.

4. A process of preparing rac-dimethyl bis(2-alkyl-1H-benz[e]indenyl)silandiyl zirconium dichloride complex which comprises condensing naphthalene with a 2-alkyl-2-propenoyl chloride after which the 2-alkyl-2,3-dihydro-1H-benz[e]indene-1-one obtained is converted to 2-alkyl-1H-benz[e]indene followed by conversion to dimethyl bis(2-alkyl-1H-benz[e]indenyl) silane, and then by conversion to rac-dimethyl bis(2-alkyl-1H-benz[e]indenyl)silandiyl zirconium dichloride complex.

5. The process of claim 1 wherein the reaction temperature is between 15° C. and −80° C.

6. A process of preparing 2-methyl-1H-benz[e]indene which comprises condensing naphthalene with a 2-methyl-2-propenoyl chloride according to the process of claim 1 after which the 2-methyl-2,3-dihydro-1H-benz[e]indene-1-one obtained is converted to 2-methyl-1H-benz[e]indene.

7. A process of preparing rac-dimethyl bis(2-methyl-1H-benz[e]indenyl)silandiyl zirconium dichloride complex which comprises condensing naphthalene with a 2-methyl-2-propenoyl chloride after which the 2-methyl-2,3-dihydro-1H-benz[e]indene-1-one obtained is converted to 2-methyl-1H-benz[e]indene followed by conversion to dimethyl bis(2-methyl-1H-benz[e]indenyl)silane, and then by conversion to rac-dimethyl bis(2-methyl-1benz[e]indenyl) silandiyl zirconium dichloride complex.

8. A process of preparing a 2-alkyl-2,3-dihydro-1H-benz[e]indene-1-one derivative which comprises condensing a naphthalene derivative with an active ester of 2-alkyl-2-propenoic acid at a reaction temperature of below 0° C.

* * * * *